United States Patent [19]
Wilk

[11] Patent Number: 5,269,753
[45] Date of Patent: Dec. 14, 1993

[54] METHOD FOR USE IN LAPAROSCOPIC HERNIA REPAIR

[76] Inventor: Peter J. Wilk, 185 W. End Ave., New York, N.Y. 10023

[21] Appl. No.: 913,601

[22] Filed: Jul. 14, 1992

[51] Int. Cl.$^5$ ............................................. A61M 31/00
[52] U.S. Cl. ......................................... 604/49; 604/23; 604/104; 604/158; 128/6; 128/747; 606/192; 606/198
[58] Field of Search ........................... 604/19, 23-25, 604/26, 27, 28, 48, 49, 93, 96, 97, 98, 99, 104-109, 158, 162, 163, 164, 170-171, 263, 51; 128/747, 749, 4, 6, 8, DIG.12, 898; 606/191-192, 108, 198, 15, 213

[56] References Cited

U.S. PATENT DOCUMENTS

| | | | |
|---|---|---|---|
| 3,817,251 | 6/1974 | Hasson | 604/26 |
| 3,882,852 | 5/1975 | Sinnreich | 128/4 |
| 4,612,938 | 9/1986 | Dietrich et al. | 606/15 |
| 4,976,710 | 5/1990 | Mackin | 606/15 |
| 5,103,804 | 4/1992 | Abele et al. | 128/4 |
| 5,116,357 | 5/1992 | Eberbach | 606/213 |
| 5,158,548 | 10/1992 | Lazarus | 606/191 |
| 5,176,692 | 1/1993 | Wilk et al. | 604/104 |
| 5,178,133 | 1/1993 | Pena | 604/108 |
| 5,183,468 | 2/1993 | Xanthakos et al. | 604/109 |
| 5,188,596 | 2/1993 | Condon et al. | 606/192 |

FOREIGN PATENT DOCUMENTS

| | | | |
|---|---|---|---|
| 9101687 | 2/1991 | PCT Int'l Appl. | |
| 0502331 | 3/1939 | United Kingdom | 128/8 |

*Primary Examiner*—Randall L. Green
*Assistant Examiner*—K. M. Reichle
*Attorney, Agent, or Firm*—R. Neil Sudol; Henry D. Coleman

[57] ABSTRACT

A method for use in laparoscopic hernia repair comprises the steps of inserting a distal end of a laparoscope through a patient's abdominal muscles to a point outside of the parietal peritoneum, and inserting through the abdominal muscles a distal end of an elongate instrument provided at that distal end with a balloon in a collapsed configuration, the balloon being transparent to optical radiation. Upon disposition of the balloon between the abdominal muscles and the peritoneum, the balloon is inflated and the instrument is subsequently manipulated from outside the patient to push the inflated balloon against connective tissues between the abdominal muscles and the peritoneum to shift the tissues to form a pre-peritoneal space. During the manipulation of the instrument with the balloon, the laparoscope is to view, through and around the inflated balloon, the connective tissues and other organic structures.

7 Claims, 2 Drawing Sheets

METHOD FOR USE IN LAPAROSCOPIC HERNIA REPAIR

BACKGROUND OF THE INVENTION

This invention relates to a method for use in laparoscopic hernia repair.

A hernia results when a person's abdominal wall is torn to form an opening. A portion of the person's internal body organs, including a portion of the peritoneal lining, is then displaced through the opening and into the inguinal tissues. Pain is generated upon the pinching of the displaced internal body organ or organs by the opening in the abdominal wall.

Although some progress has been made in simplifying hernial repair operations, for example, through the use of laparoscopic means, there is yet opportunity for improvement. Laparoscopic repair of hernias conventionally involves the insertion of a laparoscope through a trocar sleeve or laparoscopic cannula which itself traverses abdominal muscles of the patient. The laparoscope is manipulated from outside the patient to push and displace connective tissue to thereby form a pre-peritoneal space which may be enlarged and maintained in an enlarged configuration by inflation with carbon dioxide gas.

A shortcoming of this conventional laparoscopic procedure is that the light receiving surfaces at the distal end of the laparoscope become covered with organic matter, thereby interfering with the visualization of the internal structures via the laparoscope. Accordingly, the laparoscope must be periodically withdrawn to allow a cleaning of the distal end. This procedure takes time and energy and requires vigilance in maintaining the sterility of the laparoscope.

OBJECTS OF THE INVENTION

An object of the present invention is to provide an improved method for use in hernia repair operations.

Another object of the present invention is to provide an associated instrument or instrument assembly which may be used in a laparoscopic hernia repair technique.

Another, more particular, object of the present invention is to provide such a method which eliminates the necessity for continually withdrawing a laparoscope during a laparoscopic repair procedure.

A further particular object of the present invention is to provide such a method which is easy to learn and easy to use.

Other objects of the present invention will be apparent from the detailed descriptions and drawings included herein.

SUMMARY OF THE INVENTION

A method for use in laparoscopic hernia repair comprises, in accordance with the present invention, the steps of (a) inserting a distal end of a laparoscope through a patient's abdominal muscles to a point outside of the parietal peritoneum, (b) inserting through the abdominal muscles a distal end of an elongate instrument provided at that distal end with a balloon in a collapsed configuration, the balloon being transparent to optical radiation, (c) upon disposition of the balloon between the abdominal muscles and the peritoneum, inflating the balloon, (d) manipulating the elongate instrument to push the inflated balloon against connective tissues between the abdominal muscles and the peritoneum to shift the tissues to form a pre-peritoneal space, and (e) using the laparoscope during the step of manipulating to view, through and around the inflated balloon, the connective tissues.

Pursuant to another feature of the present invention, a gaseous composition is infused or dispensed into the pre-peritoneal space to expand the space and maintain it in a desired state of expansion.

Where the laparoscope is provided with a biopsy channel, the instrument with the balloon may be inserted through the laparoscopic biopsy channel.

Generally, a laparoscope and an instrument with a balloon are inserted through one or more trocar sleeves disposed in the abdominal muscles of the patient.

A method for use in hernia repair operations in accordance with the present invention eliminates the necessity for continually withdrawing a laparoscope during a laparoscopic repair procedure. Accordingly, laparoscopic hernia repair is streamlined and faciliatated.

A method in accordance with the present invention is easy to learn and easy to use.

DETAILED DESCRIPTION

Figure 1:
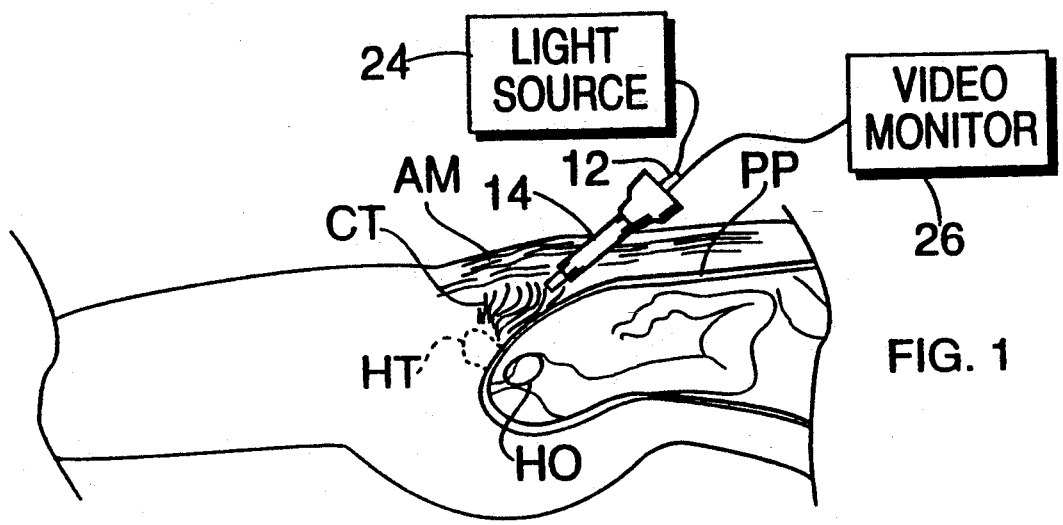
FIG. 1 is a schematic longitudinal cross-sectional view through a patient's lower trunk and upper legs, showing a trocar sleeve with a laparoscope inserted through the patient's abdominal muscles to a point outside of the peritoneum.

As illustrated in FIG. 1, a distal end of a laparoscope 12 is inserted through a patient's abdominal muscles AM to a point outside of the parietal peritoneum PP. Laparoscope 12 is inserted via a trocar sleeve or laparoscopic cannula 14 which is disposed in and traverses abdominal muscles AM pursuant to conventional techniques.

Figure 2:
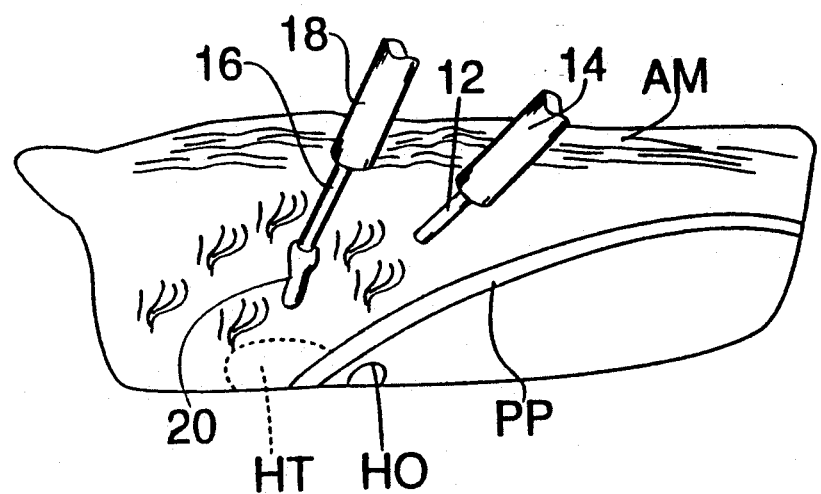
FIG. 2 is a partial schematic cross-sectional view of the patient of FIG. 1, illustrating an auxiliary instrument for clearing a peritoneal space, inserted through a second trocar sleeve traversing the abdominal muscles of the patient.

As shown in FIG. 2, a distal end of an elongate instrument 16 is inserted through abdominal muscles AM via a second trocar sleeve 18 disposed in and traversing the abdominal muscles. Instrument 16 is provided at its distal end with an inflatable balloon 20 in a collapsed configuration. Balloon 20 is transparent to optical radiation, whereby laparoscope 12 may view internal organic structures through the balloon upon inflation thereof.

Figure 3:
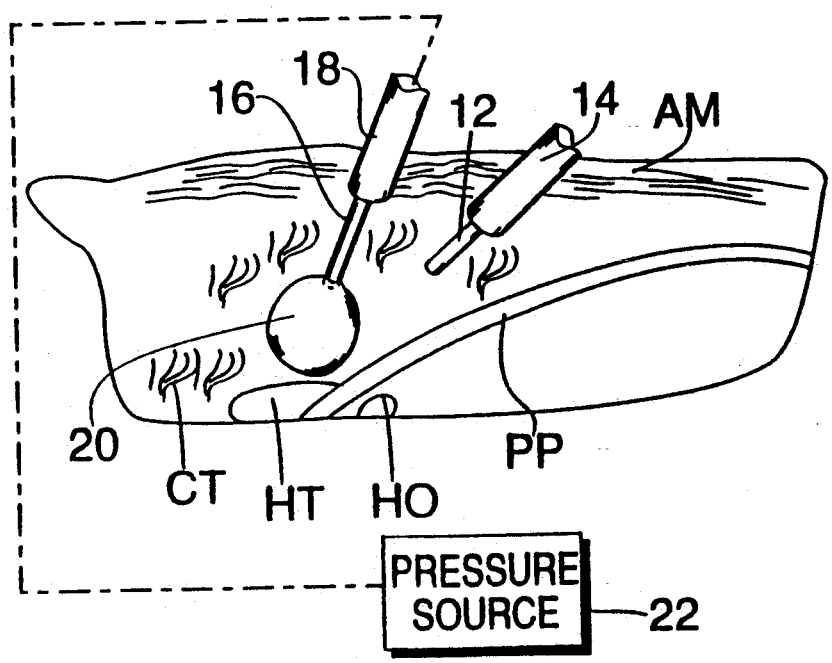
FIG. 3 is a view similar to FIG. 2, showing a balloon in an inflated configuration at the distal end of the inserted auxiliary instrument.
Figure 4:
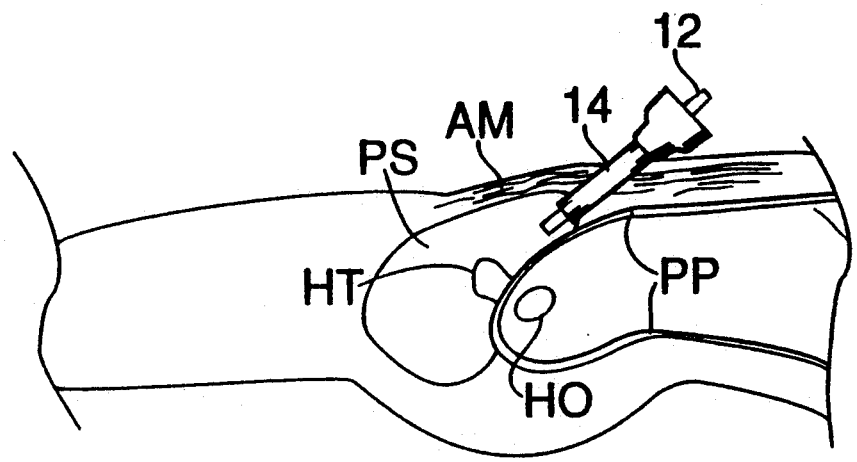
FIG. 4 is a view similar to FIG. 1, showing a pre-peritoneal space generated through use of a method in accordance with the present invention.

Upon disposition of balloon 20 between abdominal muscles AM and peritoneum PP, the balloon is inflated with a fluidic composition from a pressure source 22, as illustrated in FIG. 3. Instrument 16 is then manipulated from outside the patient to push the inflated balloon 20 against connective tissues CT between abdominal muscles AM and peritoneum PP. Balloon 20 is thereby used to displace or shift the connective tissues CT to form a pre-peritoneal space PS (FIG. 4) wherein the herniated tissues HT project via an opening HO in the peritoneum PP. During the manipulation of instrument 16, laparoscope 12 is used to visually inspect and oversee the operation. To that end, laparoscope 12 is connected to a light source 24 which supplies illuminating radiation and a video monitor 26 which presents an image of the internal organs and tissues distally of the distal end of laparoscope 12.

Pursuant to conventional laparoscopic procedures, a gaseous composition such as carbon dioxide is insufflated or dispensed into pre-peritoneal space PS to expand the space and maintain it in a desired state of expansion.

Figure 5:
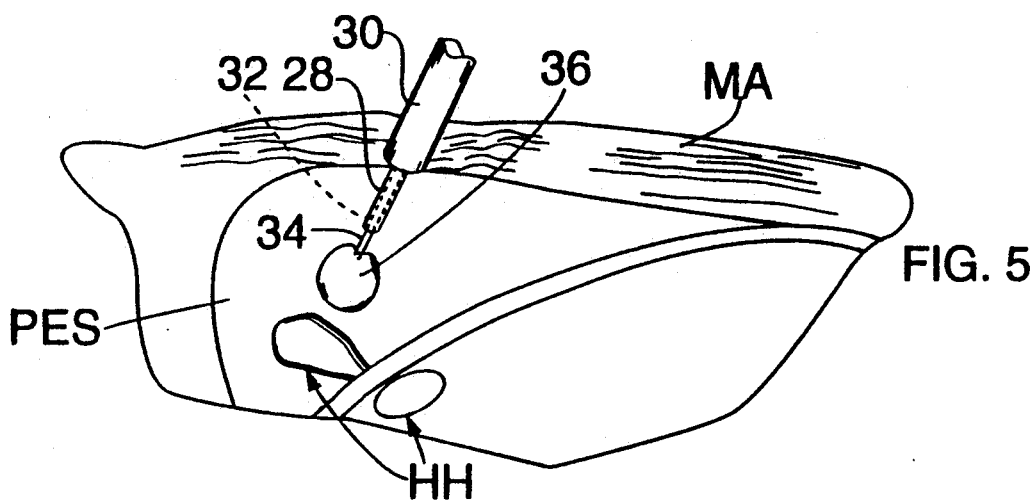
FIG. 5 is a view similar to FIG. 3, showing a stage in a modified procedure in accordance with the present invention.

As illustrated in FIG. 5, a laparoscope 28 inserted through a patient's abdominal muscles MA via a trocar sleeve or laparoscopic cannula 30 is provided with a biospy channel 32 through which an elongate instrument 34 with a balloon 36 is inserted. Balloon 36 is used to clear a pre-peritoneal space PES so that a hernia HH hay be repaired laparoscopically.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for use in laparoscopic hernia repair, comprising the steps of:

inserting a distal end of a laparoscope through a patient's abdominal muscles to a point outside of the patient's parietal peritoneum;

inserting through said abdominal muscles a distal end of a separate elongate instrument to a point between said abdominal muscles and the parietal peritoneum, said elongate instrument provided at said distal end with a balloon in a collapsed configuration, said balloon being formed of material transparent to optical radiation;

upon disposition of said balloon between said abdominal muscles and the parietal peritoneum, inflating said balloon;

manipulating said elongate instrument to push the inflated balloon against connective tissues between the abdominal muscles and the parietal peritoneum to shift said connective tissues to form a pre-peritoneal space; and using said laparoscope during said step of manipulating to view the connective tissues by optically radiating through and around the transparent material of the inflated balloon.

2. The method defined in claim 1, further comprising the step of infusing a gaseous composition into said space to expand the same.

3. The method defined in claim 2 wherein said gaseous composition is carbon dioxide.

4. The device defined in claim 1 wherein said laparoscope is provided with a biopsy channel, and wherein said step of inserting said elongate instrument further comprises inserting said elongate instrument through said biopsy channel.

5. The method defined in claim 4, further comprising the step, performed prior to said steps of inserting, of disposing a trocar sleeve in the abdominal muscles, and wherein said step of inserting said laparoscope further comprises inserting said laparoscope through said trocar sleeve.

6. The method defined in claim 1 wherein said elongate instrument with said balloon is inserted through the abdominal muscles at a point spaced from an insertion point of said laparoscope.

7. The method defined in claim 6, further comprising the step, performed prior to said steps of inserting, of disposing a trocar sleeve in the abdominal muscles, and wherein said step of inserting said elongate instrument further comprises inserting said elongate instrument through said trocar sleeve.

* * * * *